(12) United States Patent
Kern et al.

(10) Patent No.: US 8,923,578 B2
(45) Date of Patent: Dec. 30, 2014

(54) DEVICES AND METHODS FOR ASSESSING CHANGES IN CORNEAL HEALTH

(75) Inventors: Jami R. Kern, Fort Worth, TX (US); Christine Sindt, Iowa City, IA (US); Bruno Lay, Herouville Saint-Clair (FR)

(73) Assignee: Alcon Research, Ltd., Fort Worth, TX (US)

( * ) Notice: Subject to any disclaimer, the term of this patent is extended or adjusted under 35 U.S.C. 154(b) by 730 days.

(21) Appl. No.: 13/096,539

(22) Filed: Apr. 28, 2011

(65) Prior Publication Data
US 2011/0274322 A1     Nov. 10, 2011

Related U.S. Application Data

(60) Provisional application No. 61/331,983, filed on May 6, 2010.

(51) Int. Cl.
| | | |
|---|---|---|
| G06K 9/00 | (2006.01) |
| A61B 3/00 | (2006.01) |
| G06T 7/00 | (2006.01) |
| A61B 8/14 | (2006.01) |

(52) U.S. Cl.
CPC .............. *A61B 3/0025* (2013.01); *G06T 7/0012* (2013.01); *G06T 7/0028* (2013.01); *G06T 2200/24* (2013.01); *G06T 2207/10056* (2013.01); *G06T 2207/30041* (2013.01)
USPC .......................................... 382/128; 600/443

(58) Field of Classification Search
CPC ...................... G06T 7/0012; G06T 2207/3004; G06T 2200/24; G06T 2207/10056; G06T 7/0028; A61B 3/0025
USPC ........... 382/100, 128–132; 128/920; 600/101, 600/109, 112, 114, 117–118, 139, 145, 173, 600/420, 424, 427, 434; 606/1, 45
See application file for complete search history.

(56) References Cited

U.S. PATENT DOCUMENTS

| | | | | |
|---|---|---|---|---|
| 5,852,498 A | | 12/1998 | Youvan et al. | |
| 5,986,271 A | | 11/1999 | Lazarev et al. | |
| 5,988,271 A | * | 11/1999 | Oneal et al. | 166/51 |
| 6,006,756 A | * | 12/1999 | Shadduck | 128/899 |

(Continued)

FOREIGN PATENT DOCUMENTS

| | | |
|---|---|---|
| EP | 2172150 A1 | 7/2010 |
| WO | WO2010/0093772 | 8/2010 |

OTHER PUBLICATIONS

Saari; "Immunology of the lacrimal gland, tear film and ocular surface"; Book Review; Graefe's Arch. Clin. Exp. Ophthalmol; vol. 245; p. 471 (2007).

(Continued)

*Primary Examiner* — Hadi Akhavannik
*Assistant Examiner* — Mehdi Rashidian
(74) *Attorney, Agent, or Firm* — Haynes and Boone, LLP

(57) ABSTRACT

A computer-implemented method for use in assessing a cornea which includes selecting a principal image from among a series of layered images of the cornea. The computer-implemented method further includes detecting a plurality of corneal structures in the principal image and providing a quantitative analysis of the plurality of corneal structures.

27 Claims, 11 Drawing Sheets

(56) References Cited

U.S. PATENT DOCUMENTS

| | | | |
|---|---|---|---|
| 6,044,196 A | | 3/2000 | Winston et al. |
| 6,049,367 A | * | 4/2000 | Sharp et al. .................. 349/117 |
| 6,252,979 B1 | | 6/2001 | Lee et al. |
| 7,860,286 B2 | | 12/2010 | Wang et al. |
| 7,889,948 B2 | | 2/2011 | Steedly et al. |
| 8,292,878 B2 | * | 10/2012 | Arnoldussen et al. ............ 606/5 |
| 2002/0151774 A1 | | 10/2002 | Soller et al. |
| 2006/0077581 A1 | | 4/2006 | Schwiegerling et al. |
| 2006/0142662 A1 | | 6/2006 | Van Beek |
| 2008/0077581 A1 | * | 3/2008 | Drayer et al. ..................... 707/5 |
| 2008/0086048 A1 | * | 4/2008 | Dupps et al. .................. 600/405 |
| 2008/0090198 A1 | | 4/2008 | Liang et al. |
| 2008/0239070 A1 | | 10/2008 | Westwick et al. |
| 2010/0004537 A1 | * | 1/2010 | Eilers et al. .................. 600/443 |
| 2010/0004538 A1 | * | 1/2010 | Eilers et al. .................. 600/444 |
| 2010/0079580 A1 | * | 4/2010 | Waring, Iv ...................... 348/44 |
| 2010/0128960 A1 | * | 5/2010 | Yumikake ..................... 382/133 |
| 2010/0204584 A1 | | 8/2010 | Ornberg |
| 2011/0164218 A1 | | 7/2011 | Ornberg |
| 2011/0200242 A1 | * | 8/2011 | Takama et al. ................. 382/131 |
| 2011/0202044 A1 | * | 8/2011 | Goldshleger et al. ............. 606/4 |
| 2011/0262891 A1 | * | 10/2011 | Ozaki et al. ........................ 435/3 |

OTHER PUBLICATIONS

Stachs et al; "In vivo three-dimensional confocal laser scanning microscopy of the epithelial nerve structure in the human cornea"; Laboratory Investigation; Graefe's Arch. Clin. Exp. Ophthalmol; vol. 245; pp. 569-575 (2007).

Begley, et al., "Effect of lens care systems on corneal fluorescein staining and subjective comfort in hydrogel lens wearers," Clinical Article: ICLC, vol. 21, Jan./Feb. 1994, pp. 7-13.

Bron, et al., "Grading of corneal and conjunctival staining in the context of other dry eye tests," Cornea, Clinical Sciences, vol. 22, No. 7, Oct. 2003, pp. 640-650.

Dean, et al., "Clinical Technique: Documentation of corneal epithelial defects with fluorescein-enhanced digital fundus camera photography," Clinical and Experimental Ophthalmology, vol. 36, 2008, pp. 113-118.

Lemp, "Report of the national Eye Institute/Industry Workshop on Clinical Trials in Dry Eyes," CLAO, vol. 21, No. 4, Oct. 1995, pp. 221-232.

Novitskaya, et al., "Novel method to study fluorescein staining of the ocular surface using the fluorescein angiogram setting of the fundus camera," Contact Lens & Anterior Eye, vol. 30, 2007, pp. 258-259.

PCT Office, International Search Report and Written Opinion dated Apr. 7, 2010, Application No. PCT/US2010/023865, 9 pages.

* cited by examiner

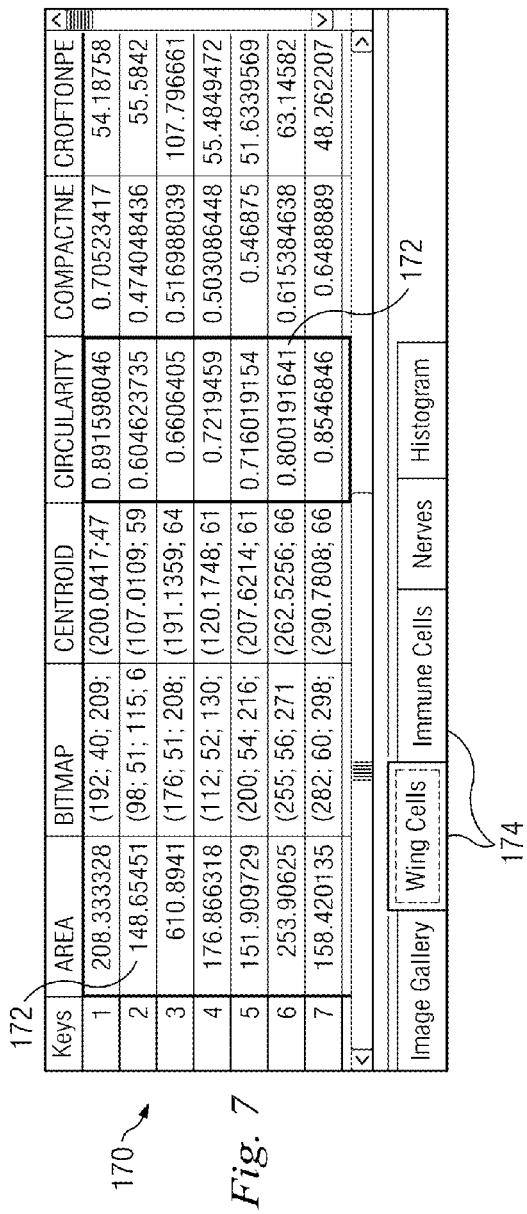

DEVICES AND METHODS FOR ASSESSING CHANGES IN CORNEAL HEALTH

CROSS-REFERENCE TO RELATED APPLICATIONS

This application claims priority to U.S. Provisional Application No. 61/331,983, filed on May 6, 2010, entitled "DEVICES AND METHODS FOR ASSESSING CHANGES IN CORNEAL HEALTH," the entire disclosure of which is incorporated herein by reference thereto.

FIELD

The application relates to a computer-implemented method for use in assessing a cornea which includes selecting a principal image from among a series of layered images of the cornea, as well as detecting a plurality of corneal structures in the principal image and providing a quantitative analysis of the plurality of corneal structures.

BACKGROUND

Corneal imaging is useful in assessing corneal health, monitoring the progression of corneal disease, and evaluating the efficacy of corneal treatments. A corneal confocal microscope is an example of an imaging device that measures characteristics of the cornea. In vivo confocal microscopy allows for high resolution, reliable, real-time imaging of the living corneal microstructure to evaluate, for example, normal corneal morphology, pathogen invasion, dystrophies and degenerations, post surgical management, dry eyes, drug toxicities, endothelial monitoring, and contact lens related changes.

A normal, healthy cornea is a transparent, avascular connective tissue made up of five layers: epithelium, Bowman's layer, stroma, Descemet's membrane, and endothelium. The corneal epithelium, the outermost layer of the cornea, is a tissue having a thickness of about 50 μm composed of 5 to 6 layers of cells. The corneal epithelium represents about one-tenth of the thickness of the cornea. The corneal epithelium can be divided into three anatomical groups: superficial cells, wing cells, and basal cells.

Superficial epithelial cells are flat polygonal cells that are stacked two to three cell layers deep on the outermost surface of the cornea. When imaged, these cells are characterized by a polygonal pattern, bright illuminated cytoplasm, a reflective nucleus and a perinuclear dark halo. As cells die, the entire cytoplasm becomes hyper-reflective. These superficial cells are up to 50 μm in diameter and about 5 μm thick. They are typically least dense in the corneal center, at around 624 cells/mm$^2$, and typically most dense in the periphery, at around 1213 cells/mm$^2$.

Immediately under (i.e., posterior to) the superficial cells are the wing cells. Wing cells are two to three cells deep. They can be divided into upper (larger) and lower (smaller), but are generally around 20 μm in size and form a regular mosaic pattern. The average density is 5000 cells/mm$^2$ in the central cornea and 5500 cells/mm$^2$ in the periphery.

The inner most layer (i.e., most posterior) of epithelial cells is the basal epithelium. These are the smallest of the epithelial cells, averaging around 8-10 μm. When imaged, they appear as a dense mosaic with highly reflective borders (tight junctions). The average density varies from 6000 to 9000 cells/mm$^2$ in the center and greater than 10,000 cells/mm$^2$ in the periphery.

The sub-basal nerve plexus is immediately adjacent to the basal epithelium. When imaged, the nerve plexus is seen as a relatively cell-free layer with parallel linear hyper-reflective fibers. The nerves are characterized by local axon enlargements which are accumulations of mitochondia and glycogen particles. The fibers are organized into a vortex pattern and therefore will run in different directions depending on the scan location.

Bowman's layer is 8-10 μm thick and consists of randomly arranged collagen fibrils located between the basal cell layer and the stroma. This layer often appears hazy and dysmorphic.

The stroma takes up 80-90% of the whole corneal volume. It consists of cellular, acellular and neurosensory structures. The cellular component (keratocytes) has reflective nuclei, whereas the acellular component (collagen lamellae) appears black or optically transparent. Keratocyte density is highest in the anterior-stroma, declines in the mid-stroma and increases slightly again towards the posterior-stroma. Stromal nerve fibers are thicker than sub-epithelial nerve fibers.

Descemet's membrane may not be visible using confocal microscopy.

The endothelium is a single layer of cells which form a hexagonal mosaic pattern. Healthy endothelium consists of 2500-3000 cells/mm$^2$, however, this decreases with age, disease, and low-oxygen transmissible contact lens wear.

Immune cells, including leukocytes, protect against foreign invaders. The main categories of leukocytes include granular (e.g., neutrophils, basophils and eosinophils), non-granular (e.g., macrophages) and lymphocytes. Granulocytes are typically very small (<10 μm) highly motile and readily invade the cornea during inflammation in response to chemotaxic factors from microbes and injured cells. Macrophages (up to 20 μm) are typically present at the ulcer site and may remain for many months within the tissue. Lymphocytes are found in the palpebral and tarsal conjunctiva. Leukocytes are typically located at the level of the basal or wing cells. Though they are not easily differentiated by confocal microscopy, location, size, and morphology may aid in identification. For example, immune cells may generally migrate along the nerve plexus. They may also, for example, be identified in the basal epithelium and Bowman's layer.

A confocal microscope works by measuring light reflected within a clear or opaque tissue. A corneal confocal microscope illuminates a small region of the cornea with a collimated light source that passes through an aperture and is focused through an objective lens to a tiny volume of space at the focal region of the lens. Reflected light from the focal region is then recollected by the objective lens. The light then passes through a beam splitter and a pinhole before entering a photodetection apparatus. The detector aperture blocks scattered light, resulting in sharper images than those from conventional light microscopy techniques. The photodetection device transforms the light signal into an electrical one, creating a digital histological image.

In vivo confocal microscopy typically has been used clinically to evaluate various corneal pathologies, including infectious keratitis (in particular, Acanthamoeba and fungal keratitis), corneal dystrophies, and other parameters of corneal health and disease. However, in vivo confocal microscopy may yield images containing a massive amount of data that may be difficult to analyze and interpret consistently and quickly. Therefore, most applications of in vivo confocal microscopy have been qualitative or have required time-consuming manual analysis to yield quantitative results. Consequently, there is a need in the art for robust and rapid image processing techniques to objectively evaluate confocal microscopy images to quantify corneal changes.

SUMMARY

This disclosure relates generally to, and encompasses, methods and computer systems, which include software, for analyzing medical images and more specifically to methods and computer systems for analyzing microscopy images to assess corneal health.

In one embodiment, a computer-implemented method for use in assessing a cornea comprises selecting a principal image from among a series of layered images of the cornea. The computer-implemented method further comprises detecting a plurality of corneal structures in the principal image and providing a quantitative analysis of the plurality of corneal structures.

In another embodiment, a computer readable medium with computer executable instructions stored thereon is used to analyze corneal structures depicted in a series of layered images of a cornea. The computer executable instructions comprise selecting a principal image from among the series of layered images of the cornea and detecting a first type of corneal structure in the principal image. The instructions further comprise providing a quantitative analysis of the first type of corneal structure in the principal image.

In another embodiment, a method for generating a three-dimensional image of a portion of a cornea comprises selecting a principal image from among a series of layered images of the portion of the cornea. The method further comprises identifying an anterior image to the principal image from among the series of layered images of the portion of the cornea and identifying a posterior image to the principal image from among the series of layered images of the portion of the cornea. The method further comprises identifying a feature of the cornea visible in each of the principal, anterior, and posterior images and registering the feature of the cornea in each of principal, anterior, and posterior images. The method further includes rendering the three-dimensional image of the portion of the cornea using at least the principal, anterior, and posterior images from among the series of layered images of the cornea.

Further aspects, forms, embodiments, objects, features, benefits, and advantages of the present invention shall become apparent from the detailed drawings and descriptions provided herein.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIGS. 7-9 are exemplary graphical displays of information about the identified nerves and cells.

DETAILED DESCRIPTION OF PREFERRED EMBODIMENTS

Figure 1:
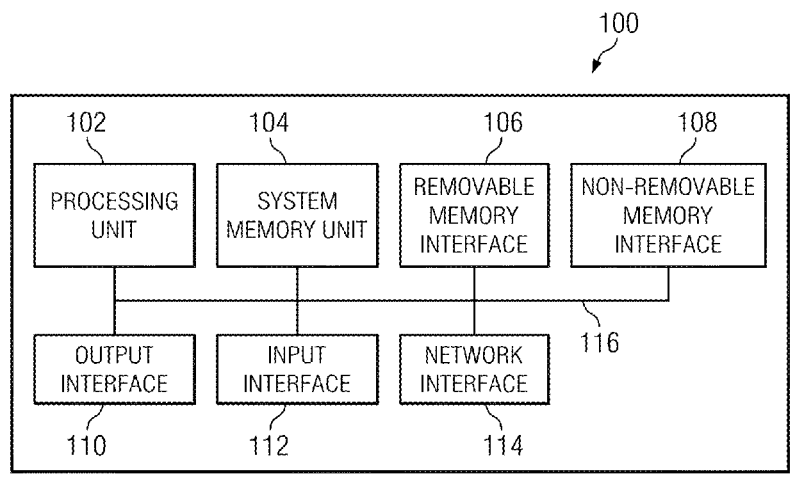
FIG. 1 is a system diagram depicting a general purpose computing device constituting an exemplary system for implementing an embodiment of the present disclosure.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

Techniques for analyzing images of biological tissues, including corneal tissue, as will be described in this disclosure, are achieved with many general purpose or special purpose computing devices, including personal computers, server computers, mobile computers, and distributed computing systems. Referring to FIG. 1, a general purpose computing device 100 constituting an exemplary system for implementing an embodiment of the present disclosure, is illustrated. The computing device 100 may include components such as a central processing unit ("CPU") 102, a system memory unit 104, a removable memory interface 106, a non-removable memory interface 108, an output interface 110, an input interface 112, and a network interface 114.

The system memory unit 104 may be volatile memory, non-volatile memory, or a combination of the two. The system memory unit 104 may be any type of computer storage media, including random access memory (RAM), read only memory (ROM), programmable ROM (PROM), erasable PROM (EPROM), electrically EPROM (EEPROM), flash memory, CD-ROM, digital versatile disc (DVD), magnetic tape, magnetic disc storage, or any other medium for storing information to be accessed by the computing device 100. Interfaces 106, 108 allow the computer to access or store information on removable or non-removable computer readable media which may be any of the types listed above.

The output interface 110 allows the computer 100 to interface with an output device such as a display, a printer, speakers, or any other device for presenting information from the computer. The input interface 112 allows the computer 100 to interface with an input device such as a keyboard, mouse, voice input device, touch input device, camera, microscope, or other device for presenting information to the computer.

The network interface 114 allows the computer 100 to interface with other computing devices or computer readable media directly or via a network. The network interface 114 may be, for example, one or more network interface cards (NICs) that are each associated with a media access control (MAC) address. The components 102, 104, 106, 108, 110, 112, 114 are interconnected by a bus system 116. It is understood that the computing device may be differently configured and that each of the listed components may actually represent several different components. For example, the CPU 102 may actually represent a multi-processor or a distributed processing system.

Figure 2:
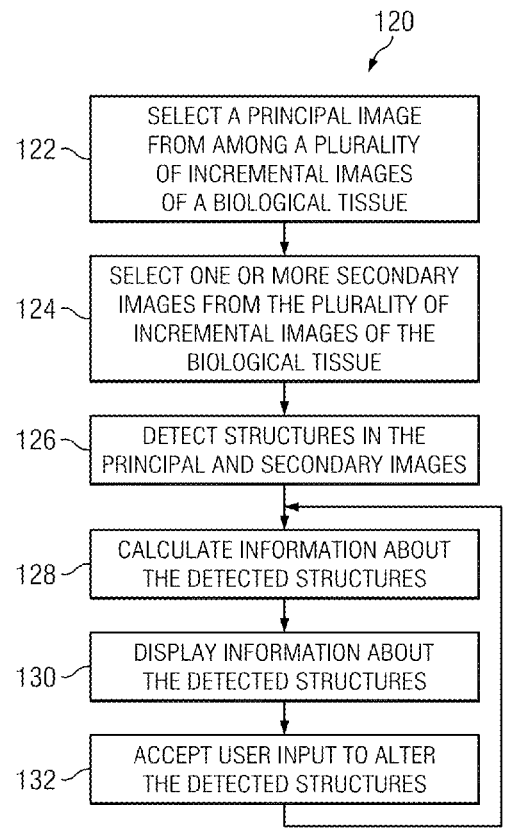
FIG. 2. is a flow diagram generally outlining one embodiment of a process for analyzing images of biological tissue.

Within any of the above described operating environments, processes for analyzing images of biological structures may be implemented. Referring now to FIG. 2, in one embodiment a process 120 for analyzing images of biological structures, including for example corneal structures, generally includes the step 122 of selecting a principal image from among a plurality of incremental images of biological tissue. At step 124, one or more secondary images are selected from the plurality of incremental images of biological tissue. At step 126, structures such as cells, cellular components, nerves, and blood vessels are detected in the principal and secondary images. At step 128, information about the structures such as number, size, location, shape, density, or a combination thereof, is calculated. At step 130, a graphical representation of the structures is displayed and may be superimposed or overlaid on the corresponding selected image. For example, a graphical representation of the boundaries of the wing cells may be displayed over the secondary image. At step 132, user input may be accepted to, for example, refine structure detection parameters or alter the graphical representations. Steps 128-132 may be repeated as desired by the user. It is understood that other embodiments of this disclosure may include additional process steps or may omit certain process steps.

Figure 3:
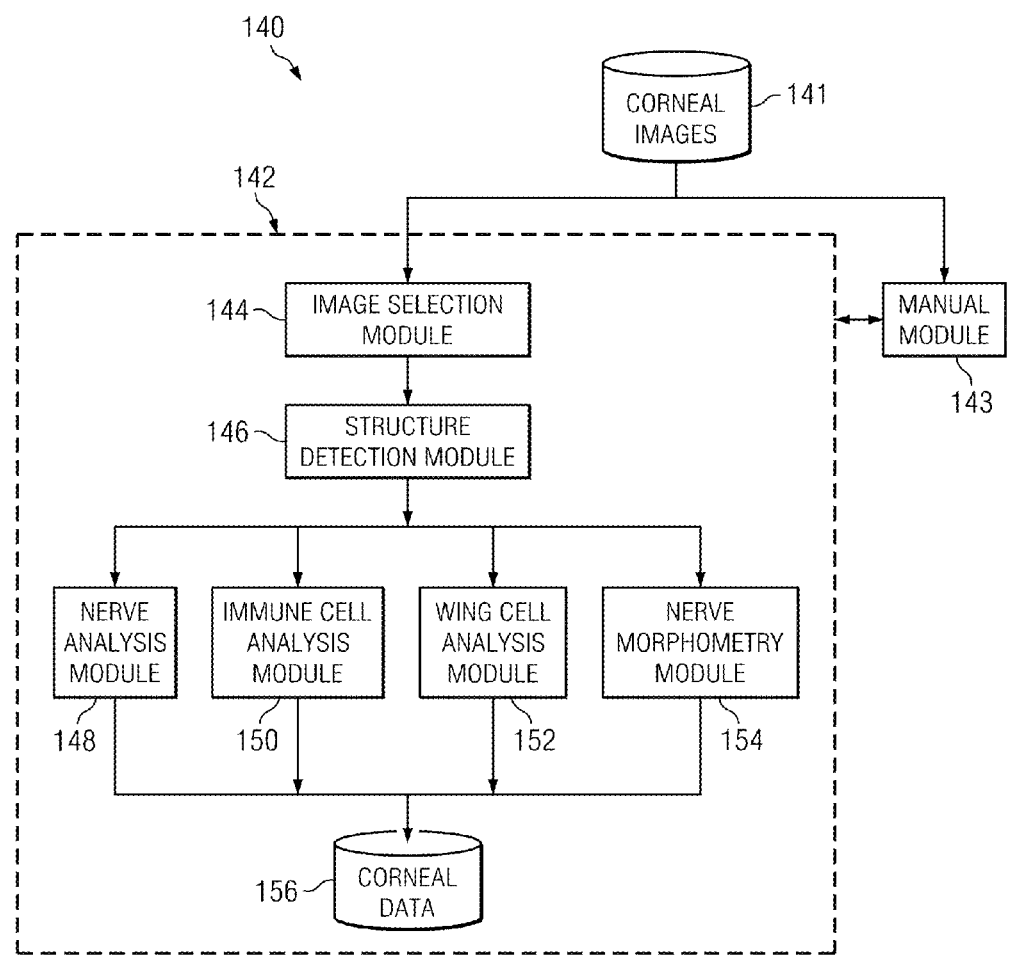
FIG. 3 is an architectural system diagram showing program modules for implementing one embodiment of the present disclosure.

The present techniques for analyzing images of biological tissues may be described in the general context of computer-executable instructions, such as program modules, being executed by a computer in combination with various software and/or hardware modules. Generally, program modules include routines, programs, objects, components, and data structures that perform specific tasks. The processes summarized above in FIG. 2 are illustrated in the architectural system diagram of FIG. 3. In particular, the system diagram of FIG. 3 illustrates the interrelationships between program modules for implementing techniques for analyzing images of a specific type of biological tissue, namely corneal tissue, as described herein. It should be understood that corneal tissue is but one type of biological tissue, and that any type of biological tissue known to those of ordinary skill in the art may be analyzed using the techniques of this disclosure. In general, as illustrated in FIG. 3, a technique 140 for analyzing corneal images begins operation by providing a set of corneal images 141 for use in either an automated image processing mode 142 or a manual image processing mode 143.

The corneal images 141 may be obtained using in vivo confocal microscopy. A Heidelberg Retina Tomograph (HRT) with a Rostock corneal module, manufactured by Heidelberg Engineering GmbH, Heidelberg, Germany, is an exemplary confocal laser scanning ophthalmoscope that may be used to acquire the corneal images. This configuration of the HRT performs in vivo corneal microscopy which visualizes corneal tissue at the cellular level. The light source of the HRT is a 670 nm diode laser (Class 1) with a 1 μm resolution. The area of each captured image is approximately 400 μm by 400 μm and the digital image size is approximately 384×384 pixels, although other in vivo confocal microscopes will have a different image size, number of images, segment size, etc. that are still encompassed within the invention. Each volume scan captured may contain approximately 40 incremental layered images over an about 80 μm depth in about 2 μm segments for every scan. The incremental images may include images of the layers of the epithelium, the nerve plexus, Bowman's layer, and the stroma. The micrometer information associated with each image may be stored and used by the software to provide all measurements in calibrated units.

In use, a lens objective portion of the HRT may be positioned at the axial center of, and in contact with, a patient's cornea. The HRT is focused on the uppermost epithelial layer of the cornea and a volume scan is initiated. The automated scan captures images as it focuses, anteriorly to posteriorly, to a depth of approximately 60 μm. It should be understood that the reverse process may alternatively be used by scanning from a posterior location to an anterior location. Multiple volume scans may be captured for the same patient in the same position. The scanning procedure may be repeated for the patient's other eye, preferably in the same direction of scan.

In the automated processing mode 142, an image selection module 144 is used to identify a principal image from among the incremental corneal images 141. In some embodiments, the principal image is identified as the image with the most prominent nerves, for example the largest nerves or the greatest number of nerves, within the focal plane. Other quantitative or qualitative criteria may also or alternatively be used to select the principal image. This principal image may also be characterized as a "best nerve image layer" or an "optimal nerve image layer." The image selection module 144 may also be used to identify a secondary image from among the incremental corneal images 141. The secondary image may be a wing cell image. In one embodiment, the wing cell image may be the image located about 20 μm anterior to the principal image. The distance between successive images may be from about 0.2 μm to about 5 μm, preferably about 0.5 μm to 4 μm, and in a more preferred embodiment about 1 μm to 3 μm. If the distance between successive images is 2 μm, the secondary image is the tenth image anterior to the principal image. In this embodiment, the selection of the secondary image depends upon the selection of the principal image. In alternative embodiments, the selection of the secondary image may be based upon other quantitative or qualitative criteria. Optionally, the selected principal or secondary images may be displayed to a user. Upon viewing the selected images, the user may elect to use a different image from among the incremental images 141 for either the principal or the secondary image. If, for example, a different secondary image is preferred, the user selected image becomes identified as the secondary image. If a principal or secondary image cannot be initially identified based upon pre-established quantitative or qualitative criteria, the software may prompt the user to select a principal or secondary image from among the incremental images 141. Alternatively, the user may manually select an image as the principal or secondary image that is different from the image selected with the automated process.

Figure 4:
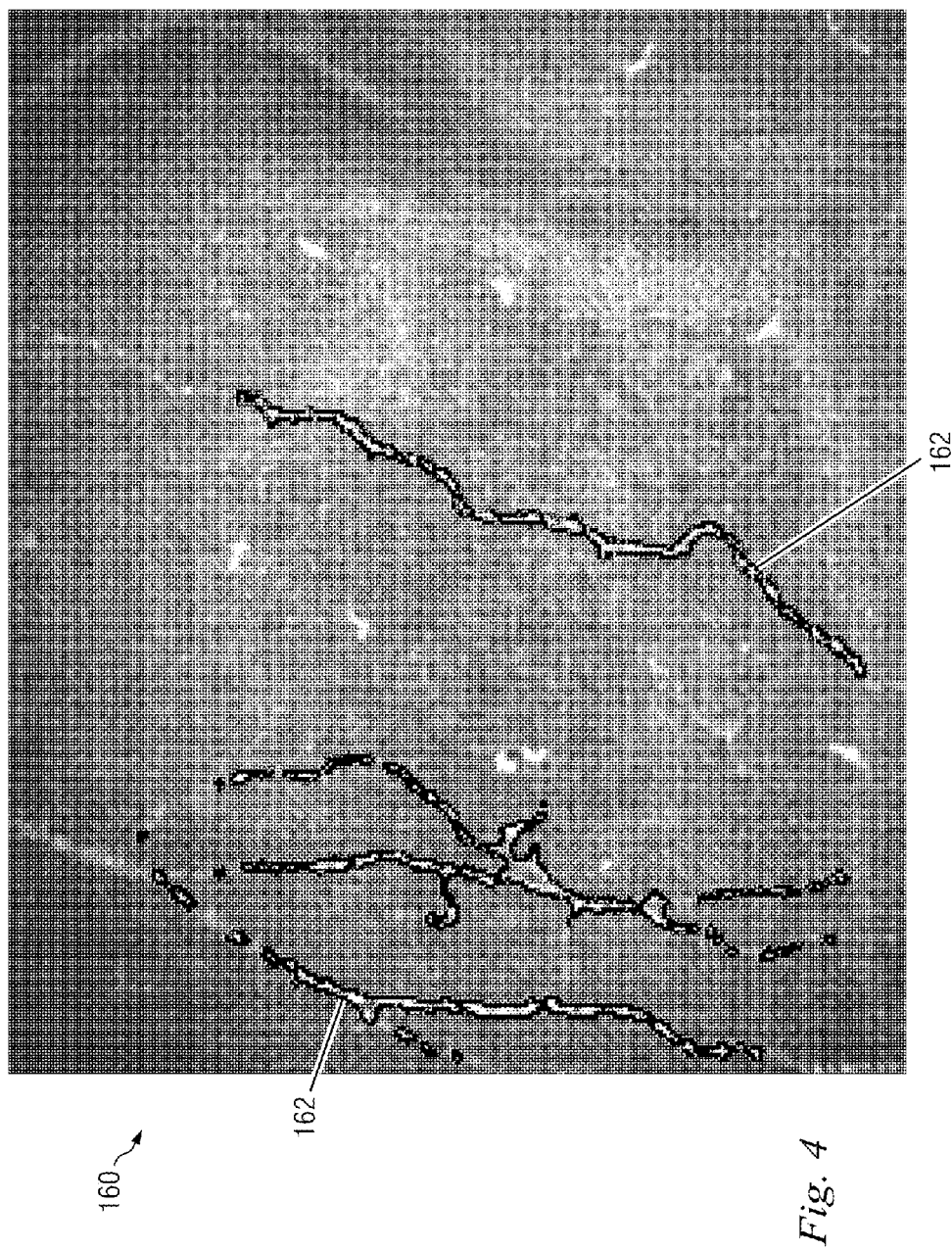
FIG. 4 is an exemplary segmented image identifying nerves in a principal image.

After the principal and secondary images are selected, a structure detection module 146 is used to graphically segment or designate structures within the selected images. The criteria for detecting structures such as nerves, immune cells, and wing cells, may be based upon attributes of the image such as brightness, shape, size, thickness, topology, identified pixel patterns, proximity to other detected structures, and correspondence to control images. Segmentation parameter values may be altered by the user for nerves or cells. As shown in FIG. 4, in a principal image 160, nerve detection is performed and results in a graphical representation 162 of tortuous lines that correspond to the detected nerves. The graphical representation 162 of the detected nerves can be displayed as an overlay to the principal image 160 to highlight, for example with color or other graphical markers, the location of the nerves in the principal image.

Figure 5:
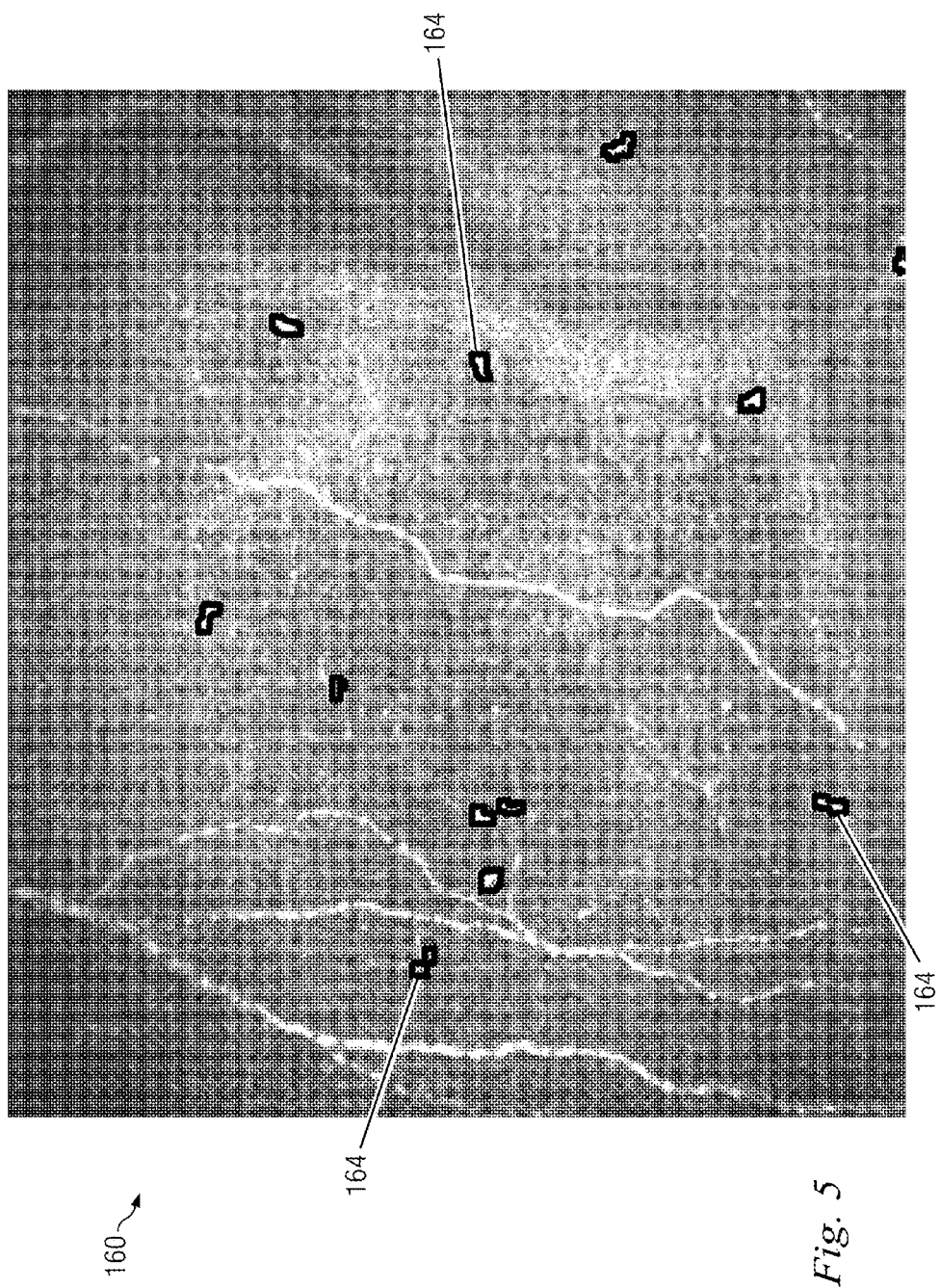
FIG. 5. is an exemplary segmented image identifying immune cells in a principal image.

As shown in FIG. 5, in the principal image 160, immune cell detection is performed and results in a graphical representation 164 of discrete regions that corresponds to the borders of detected immune cells. The graphical representation 164 of the detected immune cells can be displayed as an overlay to the principal image 160 to highlight, for example with color or other graphical markers, the location of the immune cells in the principal image. Alternatively, immune cell detection may be performed on a different image in the series of corneal images. This different image may be acquired, for example, using another time exposure.

Figure 6:
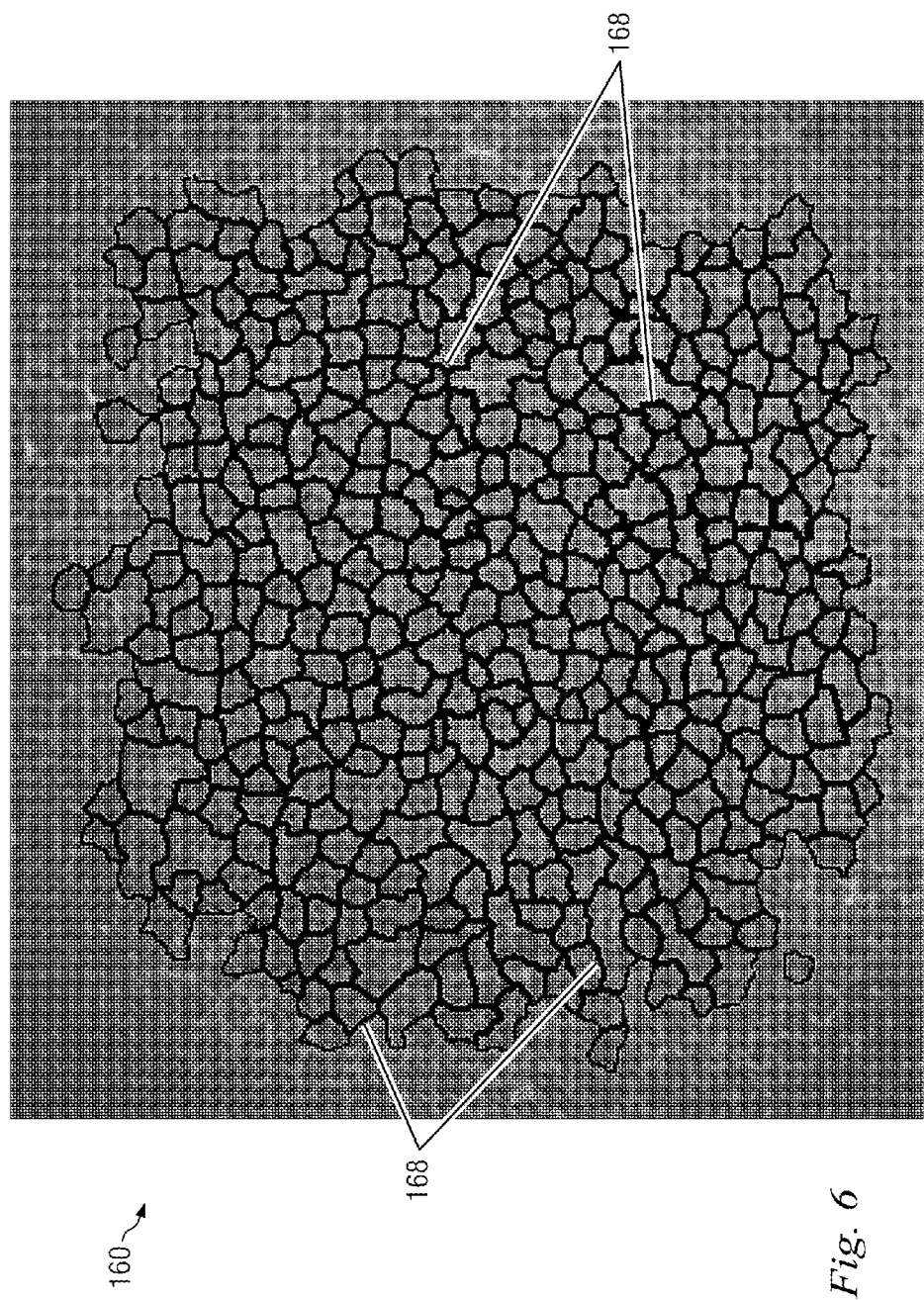
FIG. 6 is an exemplary segmented image identifying wing cells in a secondary image.

As shown in FIG. 6, in the secondary image 166 of the selected wing cell layer, wing cell detection is performed and results in a mosaic-like graphical representation 168 that corresponds to the borders of detected wing cells. The graphical representation 168 of the detected wing cells can be displayed as an overlay to the secondary image 166 to highlight, for example with color or other graphical markers, the location of the wing cells in the secondary image.

After the structures in the principal and secondary images are detected and graphically segmented, modules 148, 149, 150 are used to quantitatively analyze the detected structures. The quantitative analysis may be compared to control images and measurements, including control images from healthy or unhealthy corneas. In the nerve analysis module 148, measurements are made for each of the identified nerve structures, and attributes of the identified nerve structures and the collection of nerve structures in a region of interest are computed. Such measurements and attributes may include, for example, length, thickness, number of nerves, and number of branches, as well as combinations thereof. The nerve analysis module 148 may allow for user post-processing editing. For example, if based upon viewing the graphical representation 162 of the nerves or based upon viewing the computed attributes, the user determines that the automated graphical representation 162 should be altered or improved, the user may edit the graphical representation by deleting graphics, adding graphics, adding annotations, or filling in gaps in the tortuous lines that represent the nerves. After the graphical representations have been altered, the attributes of the identified nerve structures can be recomputed based upon the altered segmentation.

In the immune cell analysis module 150, measurements are made for each of the identified immune cells, and attributes for the individual immune cells and the collection of cells in a region of interest are computed. Such measurements and attributes may include the number of immune cells, density (number of immune cells in the region of interest), area of individual cells, mean surface area of cells in region of interest, proximity to nerves, width, pixel count, and shape factors, as well as combinations thereof. The immune cell analysis module 150 may allow for user post-processing editing. For example, if based upon viewing the graphical representation 164 of the immune cells or based upon viewing the computed attributes, the user determines that the automated graphical representation 164 should be altered or improved, the user may edit the graphical representation by doing one or more of the following: deleting graphics, adding graphics, separating graphics, or adding annotations that represent individual immune cells. After the graphical representation have been altered, the attributes of the identified immune cells can be recomputed based upon the altered segmentation.

In the wing cell analysis module 152, measurements are made for each of the identified wing cells, and attributes of the individual wing cells and the collection of wing cells in a region of interest are computed. Such measurements and attributes may include the number of wing cells, density (number of wing cells in the region of interest), average size, standard deviation, number of cells below a predefined or user established threshold and density, number of cells above a predefined or user established threshold and density, and combinations thereof. Measurements and attributes for individual cells may further include centroid, Crofton perimeter, compactness, and circularity, and combinations thereof. For the collection of wing cells in the region of interest, a region mean, a region minimum, and a region maximum may be calculated. The measurements and calculations may be performed on cells falling between minimum and maximum thresholds that are either predefined or defined by a user. The wing cell analysis module 152 may allow for user post-processing editing. For example, if based upon viewing the graphical representation 168 of the wing cells or based upon viewing the computed attributes, the user determines that the automated graphical representation 168 should be altered or improved, the user may edit the graphical representation by deleting graphics, adding graphics, adding annotations, and redrawing segmentation lines. For example, if a boundary is added to the graphical representation to split a previously identified wing cell, the module 152 will recompute all measurements and provide updated information. The wing cell analysis module 152 may also provide assistance tools to ensure that no wingcell is skipped for annotation.

Figure 9:
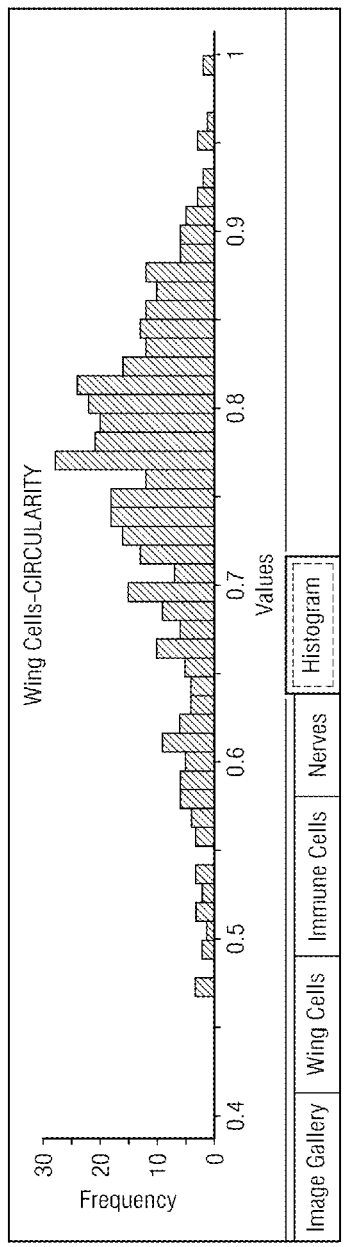

Any of the modules 143-152 may produce information 156 about the imaged cornea. Graphical user interfaces (GUI's) may be used to display information 156 to a user for any of the modules. For example, as shown in FIG. 7, a GUI 170 may include a grid for displaying information 172 about individual wing cells measured and computed in module 152. Selection tabs 174 allow a user to toggle between information displays for each of the structure analyses and summary analyses. FIG. 8 is an example of a GUI 176 that presents summary information 178 based upon the analysis performed in the analysis modules 148-152. FIG. 9 is an example of a graphical data display 180, which in this case is a histogram, that plots an attribute of the analyzed nerves or cells. Other types of graphical displays including charts, tables, spreadsheets, graphs, or data listings may be suitable for displaying data about the imaged cornea. For measurements displayed in a grid format, for example, the data may be sorted by column or row. Image synchronization may be available between the displayed data and the image.

Figure 11:
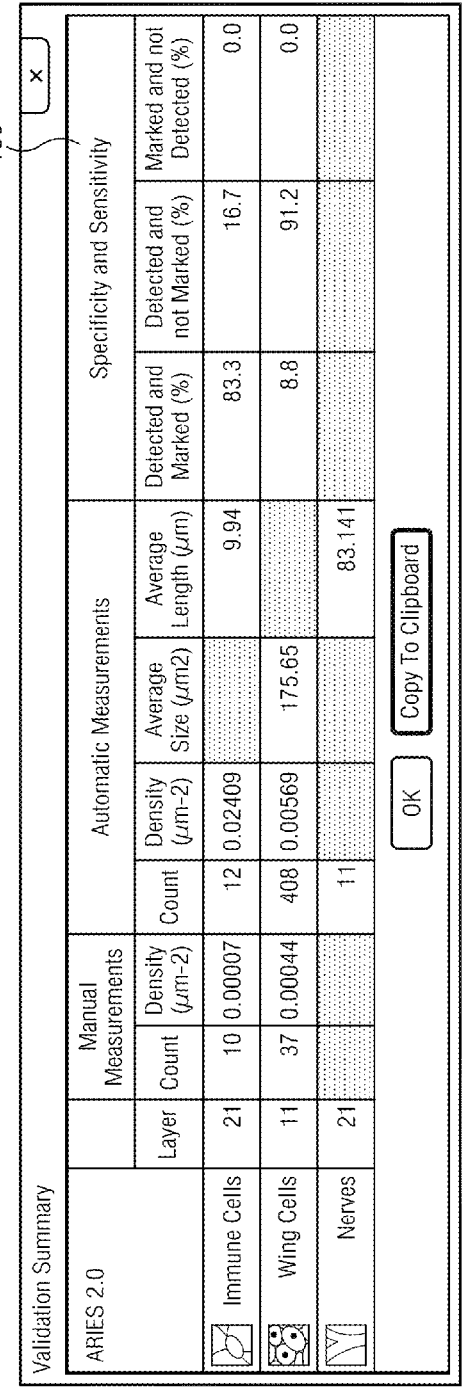
FIG. 11 is an exemplary graphical display comparing data from automated and manual modes.
Figure 10:
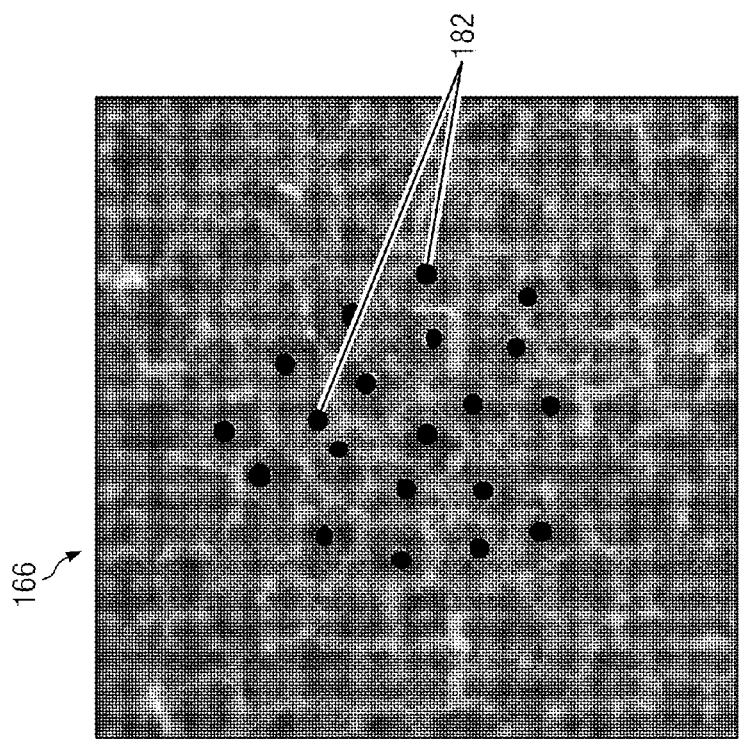
FIG. 10 is an exemplary image of manually created graphics overlaid on the secondary image.

The automated image processing mode 142, discussed above, provides automated techniques for generating graphical representations and analyzing corneal structures. The technique 140 for analyzing corneal images also includes the manual image processing mode 143 to allow the user to generate graphical representation and annotations that may be displayed with or as an alternative to the graphical representations generated in the automated image processing mode 142. The user may use modules from both the manual and automated modes to produce a desired graphical or computed set of corneal data 156. As shown in FIG. 10, for example, within the manual mode 143, the user can add annotations to the secondary image 166. For example, the user may draw graphical points 182 that correspond to user identified wing cells. The automated mode 142 may accept the user annotations 182 and use them to generate a cell count, density or other calculations about the manually identified cells. The manual counting and density information may be displayed in table form in a GUI. Additionally, the manual information may be used for comparison to automated data generated for the same region of interest. Additionally, for example, the graphical representation 168 of the wing cells and the manual annotations 182 may both be overlaid on the secondary image 166 of the wing cell layer to provide a multi-layer composite image. It is understood that similar manual mode operations may be used to annotate and compare calculations for immune cell and nerve structure analyses. As shown in FIG. 11, a GUI in the form of a validation summary table 184 may display values associated with manual measurements from the manual mode 143 and with automated measurements from the automated mode 142. A section 186 of the table 184 provides comparison information for the automated and manual modes. For example, the section 186 may display a comparison of automatically detected cells and manually marked cells, a comparison of automatically detected cells with no manual mark cells, and a comparison of manually marked and not detected cells. Sensitivity and specificity may be computed to compare manual and automatic counting.

Figure 12:
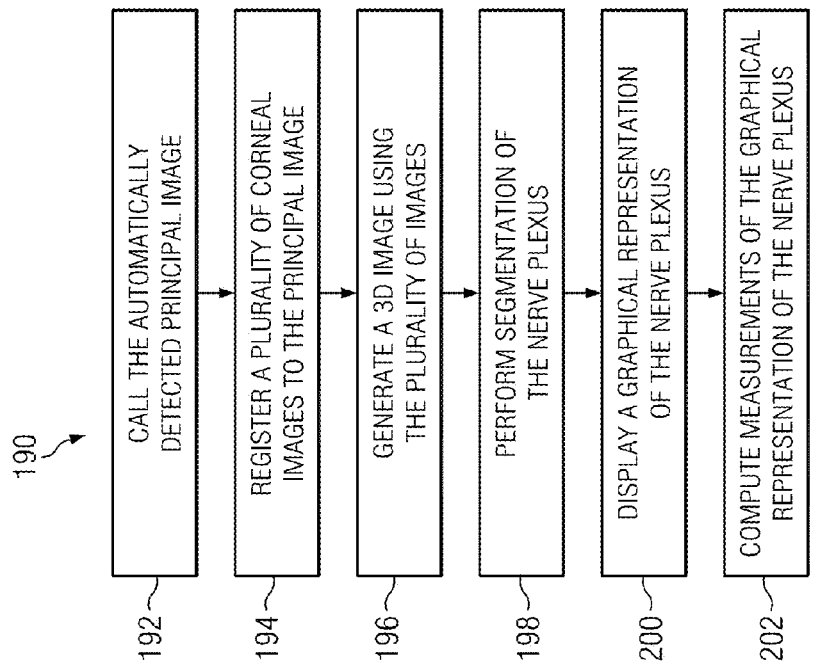
FIG. 12 is a flow diagram generally outlining one embodiment of a process for three-dimensional rendering of corneal images.

The automated image processing mode 142, further includes a nerve morphometry module 154 for generating a three-dimensional (3D) reconstruction of the nerve plexus from the corneal images 141. The nerve morphometry module 154 allows a user to assemble a subset of the corneal images 141 as a 3D object made of volumetric pixels (voxels). From this assembly, the 3D nerve plexus may be extracted and nerve measurements may be performed. As shown in FIG. 12, a method 190 that may be invoked by the nerve morphology module 154 includes the step 192 of retrieving the principal image identified in the image selection module 144.

Because nerves have configurations that change in the anterior-posterior direction, the image of the same nerve is different in successive corneal images. Eye movements can further complicate the identification of the same nerve through successive corneal images. At step 194, an image registration process identifies corresponding reference points and structures in successive corneal images. Images at a specific distance from the principal image, for example, 4 µm anterior and 4 µm posterior, may be registered to the principal image. Additional images may also be registered to the anterior and posterior images. Registration may be performed for all of the corneal images 141 or a subset. Reference points that may be used for registration include, for example, branching points of nerves, nerve extremities, or immune cells. Optionally, the user may intervene in the registration process to manually select or change registration points. The registration step 194 may be conducted, for example, in less than approximately 10 seconds. Registered images with associated rotation matrix data may be saved to disk. The nerve morphology module 154 may provide a blend function to allow the user smoothly view successive images during the registration process. Further tools such as cropping tools may be provided in the registration process to remove black background pixels (or voxels) or delete characters on each image. Further tools such as browsing tools may allow the user to play the corneal images both before and after registration as a two-dimensional video in a display.

At step 196, a 3D object is generated by stacking the registered images above and below the principal image. For example, five images anterior and five images posterior may be stacked to generate the 3D object. The gap between two sections may be user defined. In some embodiments, the 3D object can be rendered in approximately one second or less. In some embodiments, immune cells may be reconstructed with the nerves. Although nerve detection may be performed in the 3D image, immune cells may be preferably identified in the principal image. As will be discussed below, the 3D object may be displayed using one or more alternative modes of 3D rendering. In any of the alternative display modes, zooming and panning tools may be provided.

Figure 13:
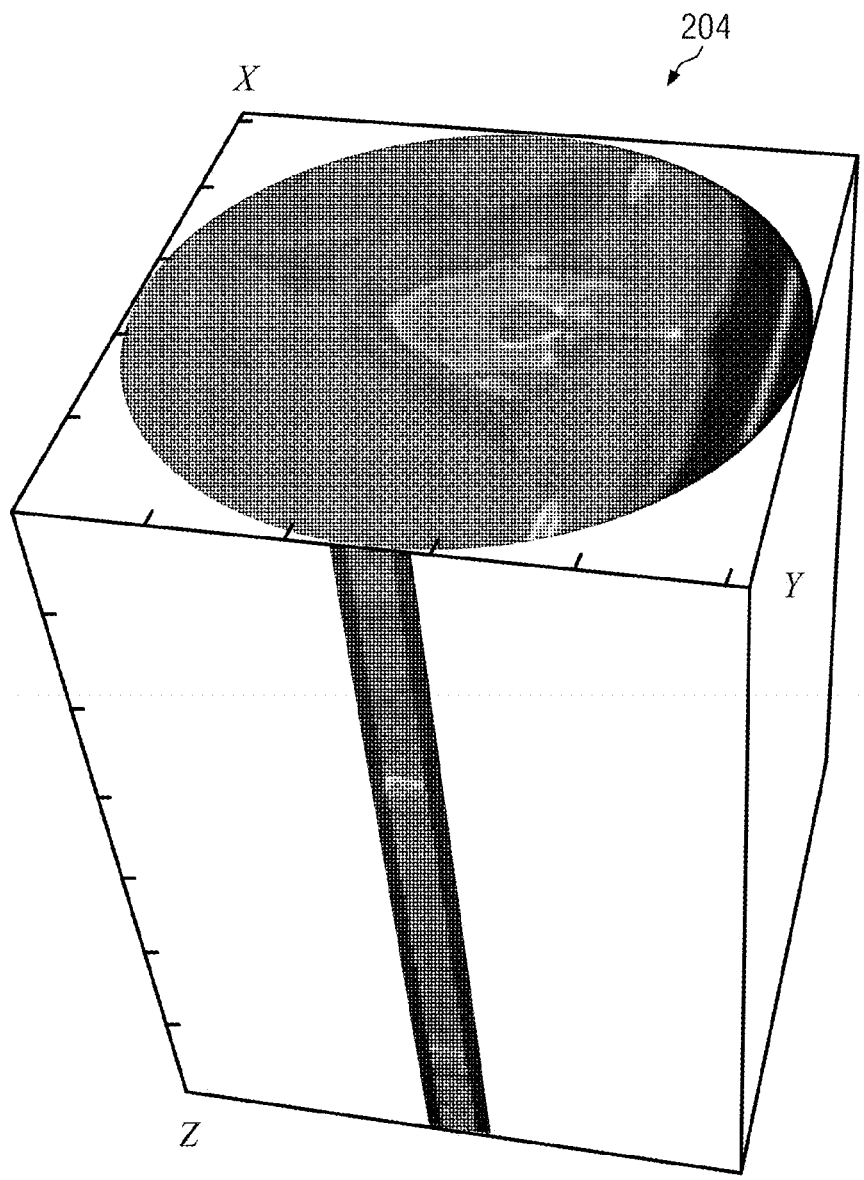
FIG. 13 is an exemplary 3D image in composite mode.

As shown in FIG. 13, the stacked and registered images can be displayed as a composite/volume mode image 204 that is freely rotatable in 3D space. The volume mode image may be displayed using full pixel (or voxel) information, including transparency. In other words, a volume rendering is performed using transmitted light information. It may be possible to view inside 3D volumes by controlling the transparency or opacity parameters, also known as alpha parameters. The opacity and color values may be controlled using a GUI and user inputs.

Figure 14:
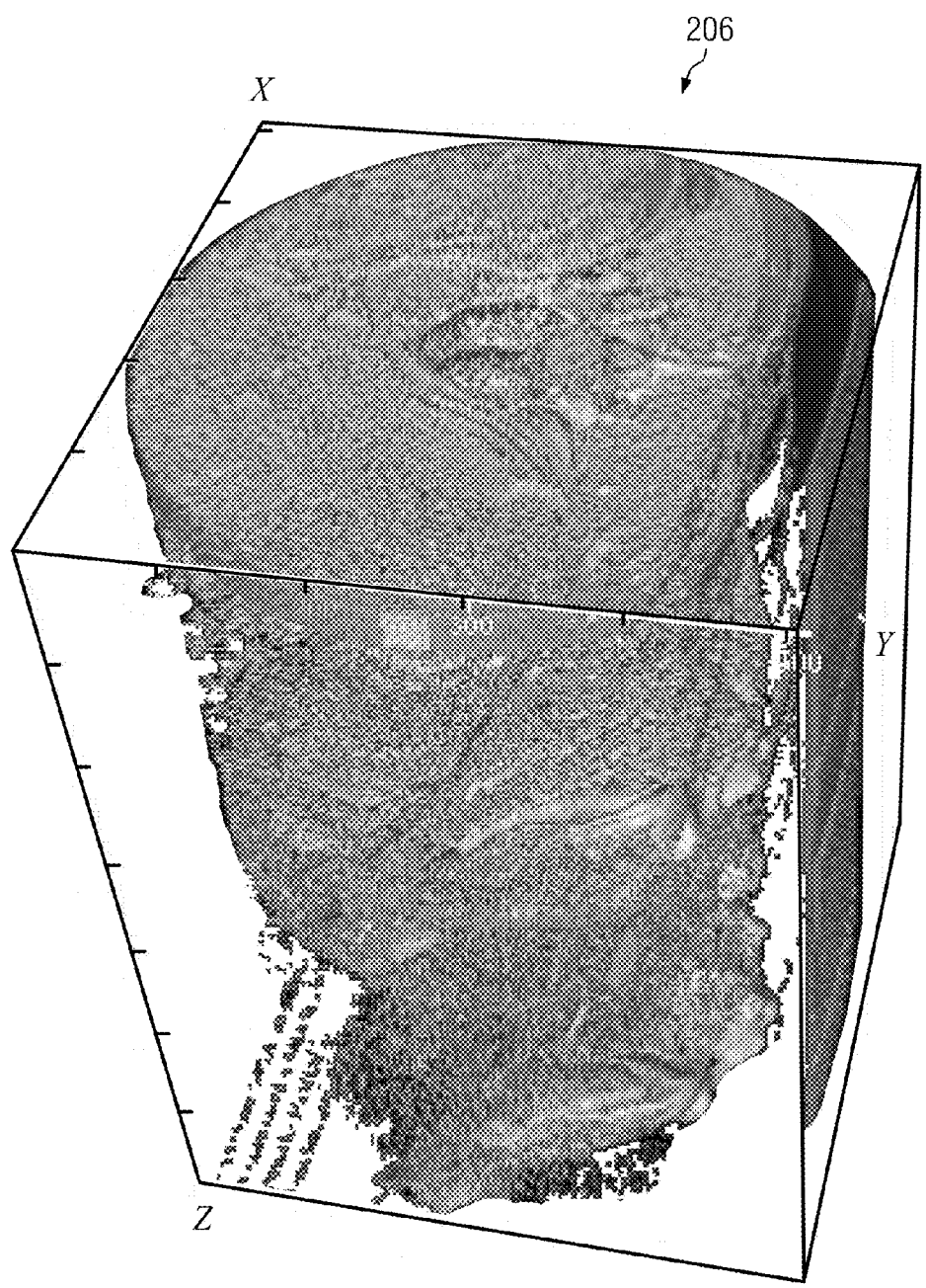
FIG. 14 is an exemplary 3D image in isosurface mode.

As shown in FIG. 14, the stacked and registered images may be displayed as an isosurface mode image 206 that is freely rotatable in 3D space. In the isosurface mode, an object is displayed using only the pixels with a value specified by the user. In other words, the image is of the surface of the object. The surfaces displayed in the isosurface mode are defined by connecting pixels belonging to the same regions and conducting interpolation using neighboring pixels.

Figure 15:
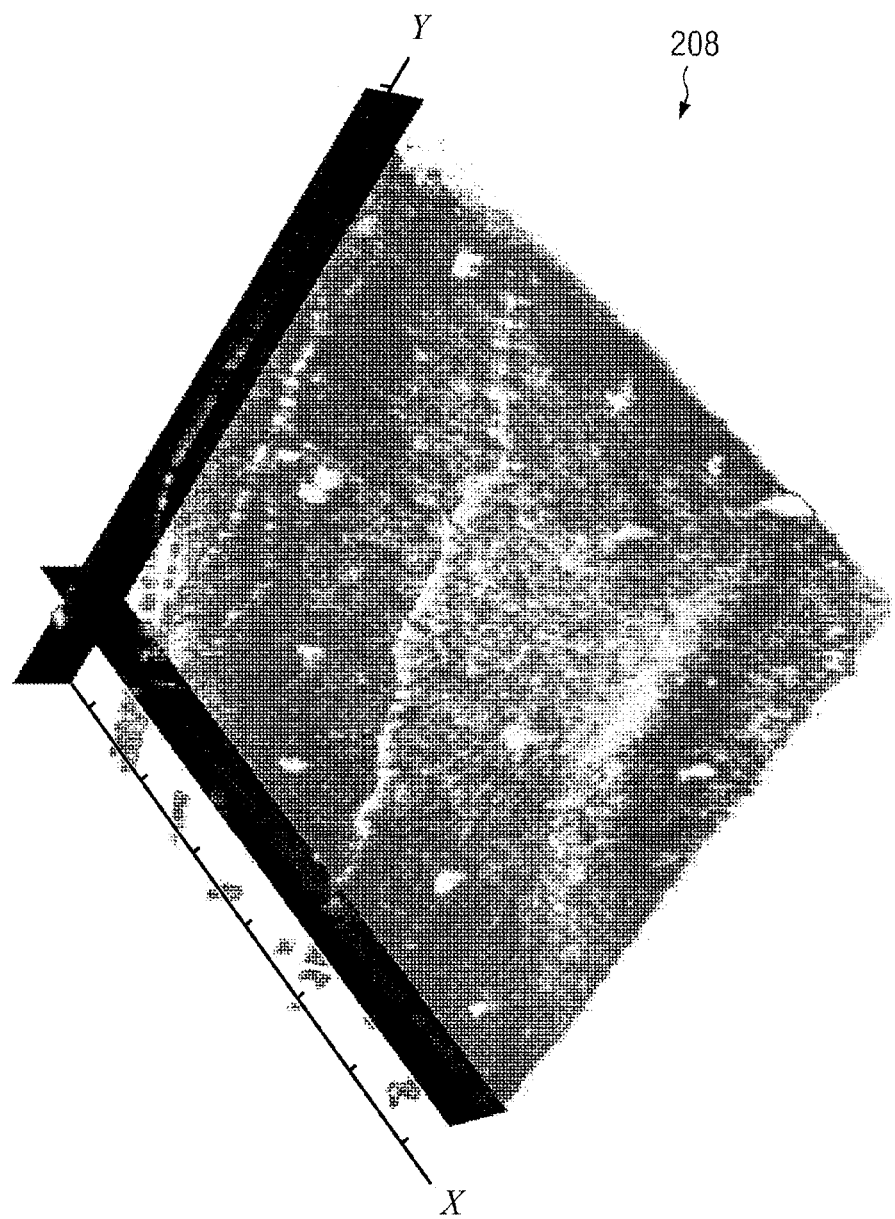
FIG. 15 is an exemplary 3D image in slice mode.

As shown in FIG. 15, the stacked and registered images may be displayed in a slice mode image 208 that is freely rotatable in 3D space. This mode allows a user to select a section plane to be displayed. The user may define the slice orientation through inputs to a GUI. More than one section may be displayed, and the distance between the multiple sections may be specified.

Referring again to FIG. 12, at step 198, segmentation is performed by processing voxels corresponding to nerves and immune cells identified either on the 3D reconstructed image or on each of the two-dimensional images in the stacked image. At step 200, a 3D graphical representation of the segmented nerves is displayed. For all rendering modes, an audio-video interleave (AVI) file may be generated by recording multiple positions of the 3D object and interpolating between successive positions. The AVI format may support codec compression. An animated video file results. At step 202, measurements of the 3D "skeleton" of the nerve plexus are computed and may include one or more of the number of branching points, the length of the branches, the thickness of the nerves, the total number of nerves, and the tortuosity of the branches. In one embodiment, the tortuosity may be calculated as the length of the branch divided by the Euclidean distance between the two extremities of the branch. For some calculations, the bottom points of the nerves may be specified. Any branch of the skeleton may be manually selected by the user in the image, and the corresponding row with measurements may be highlighted in the related measurement grid to provide the user with information about the selected branch. As previously described for the two dimensional images, a variety of charts, statistics, histograms and other graphical forms of information presentation may be generated for the 3D image. For any of the two dimensional or three dimensional modules, the various graphical forms of presented information may be exported into spreadsheets, tables or other commonly used formats compatible with and importable into commercially available spreadsheet, word processing, database, and/or presentation software.

The technique 140 for analyzing corneal images potentially has multiple applications. For example, it may be used to assess immune cell response in the corneas of contact lens wearers as compared to nonwearers, of contact lens wearers using different types of lens care solutions, and of patients with keratitis, infectious disease, or allergies. The technique 140 may also be used to assess wing cell changes in the corneas of patients with bullous keratopathy, of patients treated with eye drops that contain preservatives, and of patients with progressive epithelial corneal dystrophies. The technique 140 may also be used to assess corneal changes in patients after corneal refractive surgery or in patients with dry eye syndrome.

The term "such as," as used herein, is intended to provide a non-limiting list of exemplary possibilities.

The term "approximately" or "about," as used herein, should generally be understood to refer to both numbers in a range of numerals. Moreover, all numerical ranges herein should be understood to include each whole integer and tenth of an integer within the range.

While various embodiments of the invention have been described above, it should be understood that they have been presented by way of example only, and not limitation. Where methods and steps described above indicate certain events occurring
in certain order, those of ordinary skill in the art having the benefit of this disclosure would recognize that the ordering of certain steps may be modified and that such modifications are in accordance with the variations of the invention. Additionally, certain
steps may be performed concurrently in a parallel process when possible, as well as performed sequentially as described above. Thus, the breadth and scope of the invention should not be limited by any of the above-described embodiments, but should
be defined only in accordance with the following claims and their equivalents. While the
invention has been particularly shown and described with reference to specific embodiments thereof, it will be understood that various changes in form and details may
be made.

What is claimed is:

1. A computer-implemented method for use in assessing a cornea, which comprises:
   automatically selecting a principal image of the cornea for quantitative analysis from among a series of layered two-dimensional images of the cornea based on selection criteria met by at least one corneal structure in the principle image, wherein selecting a principal image comprises selecting an image with the most prominent nerves from among the series of layered two-dimensional images;
   detecting a plurality of corneal structures in the selected principal image based on attributes of the principle image that represent the plurality of corneal structures; and
   quantitatively analyzing the principle image by automatically computing quantitative attributes of at least one corneal structure of the detected plurality of corneal structures.

2. The computer-implemented method of claim 1 wherein the series of layered two-dimensional images comprises a series of layered confocal microscopy images of the cornea.

3. The computer-implemented method of claim 1 wherein the plurality of corneal structures comprises a plurality of nerves.

4. The computer-implemented method of claim 1 wherein the plurality of corneal structures comprises a plurality of immune cells.

5. The computer-implemented method of claim 1 which further comprises selecting a secondary image from among the series of layered two-dimensional images of the cornea and detecting a plurality of wing cells in the secondary image.

6. The computer-implemented method of claim 1 which further comprises displaying a graphical representation of the plurality of corneal structures.

7. The computer-implemented method of claim 6 which further comprises receiving user input and modifying the graphical representation of the plurality of the corneal structures in response to the user input.

8. The computer-implemented method of claim 1 which further comprises generating a three-dimensional view of at least one of the plurality of corneal structures.

9. The computer-implemented method of claim 1 which further comprises selecting an anterior image and a posterior image to the principal image from among the series of layered two-dimensional images of the cornea, and registering a common reference point in each of the principal, anterior, and posterior images.

10. The computer-implemented method of claim 1 wherein the at least one corneal structure comprises at least one nerve and wherein the selection criteria comprises at least one of a size and a quantity of the at least one corneal structure.

11. A non-transitory computer readable medium with computer executable instructions stored thereon adapted to analyze corneal structures depicted in a series of layered two-dimensional images of a cornea, the computer executable instructions which comprise:
   selecting a principal image from among the series of layered two-dimensional images of the cornea for quantitative analysis based on selection criteria met by at least one corneal structure in the principle image, wherein selecting a principal image comprises selecting an image with the most prominent nerves from among the series of layered two-dimensional images;
   detecting a first type of corneal structure in the principal image based on attributes of the principal image that represent the first type of corneal structure; and
   quantitatively analyzing the first type of corneal structure in the principal image by automatically computing quantitative attributes of the first type of corneal structure.

12. The computer readable medium of claim 11 wherein the first type of corneal structure comprises nerves.

13. The computer readable medium of claim 11 wherein the first type of corneal structure comprises immune cells.

14. The computer readable medium of claim 11 wherein the computer executable instructions further comprise selecting a secondary image from among the series of layered two-dimensional images and detecting a plurality of wing cells in the secondary image.

15. The computer readable medium of claim 14 wherein selecting a secondary image includes selecting an image approximately 20 µm anterior to the principal image from among the series of layered two-dimensional images.

16. The computer readable medium of claim 11 wherein the computer executable instructions further comprise displaying a graphical representation of the first type of corneal structure.

17. The computer readable medium of claim 11 wherein the computer executable instructions further comprise generating a three-dimensional image including at least the principal image.

18. The computer readable medium of claim 17 wherein the three-dimensional image further comprises an anterior image and a posterior image to the principal image selected from among the series of layered two-dimensional images of the cornea.

19. The computer readable medium of claim 18 wherein generating the three-dimensional image comprises registering a common reference point in each of the principal, anterior, and posterior images.

20. A method for generating a three-dimensional image of a portion of a cornea, which comprises:
    selecting a principal image from among a series of layered two-dimensional images of the portion of the cornea based on selection criteria met by at least one corneal structure in the principal image, wherein selecting a principal image comprises selecting an image with the most prominent nerves from among the series of layered two-dimensional images;
    identifying an anterior image to the principal image from among the series of layered images of the portion of the cornea;
    identifying a posterior image to the principal image from among the series of layered images of the portion of the cornea;
    identifying a feature of the cornea visible in each of the principal, anterior, and posterior images;
    registering the feature of the cornea in each of principal, anterior, and posterior images; and
    rendering the three-dimensional image of the portion of the cornea using at least the principal, anterior, and posterior images from among the series of layered images of the cornea.

21. The method of claim 20 wherein rendering the three-dimensional image comprises rendering the three-dimensional image in a composite/volume mode.

22. The method of claim 20 wherein rendering the three-dimensional image comprises rendering the three-dimensional image in an isosurface mode.

23. The method of claim 20 wherein rendering the three-dimensional image comprises rendering the three-dimensional image in a slice mode.

24. The method of claim 20 which further comprises providing a quantitative analysis of the portion of the cornea.

25. The method of claim 20 wherein the portion of the cornea comprises a nerve plexus.

26. The method of claim 25 which further comprises graphically segmenting nerves in the nerve plexus.

27. The method of claim 25 which further comprises graphically segmenting immune cells proximate to the nerve plexus.

* * * * *